(12) United States Patent
Changaris et al.

(10) Patent No.: US 10,350,187 B2
(45) Date of Patent: *Jul. 16, 2019

(54) METHODS AND COMPOSITION FOR SUPPRESSION OF PATHOGENIC BACTERIAL GROWTH, FUNGAL GROWTH, OR MICROBIAL GROWTH IN OR ON SKIN

(71) Applicant: David Changaris, Louisville, KY (US)

(72) Inventors: David G. Changaris, Louisville, KY (US); Kelly Sullivan, Louisville, KY (US)

(73) Assignee: David G. Changaris, Louisville, KY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/133,793

(22) Filed: Sep. 18, 2018

(65) Prior Publication Data

US 2019/0117608 A1    Apr. 25, 2019

Related U.S. Application Data

(63) Continuation-in-part of application No. 15/793,978, filed on Oct. 25, 2017, now Pat. No. 10,105,332, which is a continuation of application No. 15/788,798, filed on Oct. 19, 2017, now Pat. No. 10,052,300.

(51) Int. Cl.
*A61K 31/202* (2006.01)
*A61K 9/00* (2006.01)
*A61K 31/198* (2006.01)
*A61K 31/455* (2006.01)

(52) U.S. Cl.
CPC .......... *A61K 31/202* (2013.01); *A61K 9/0014* (2013.01); *A61K 31/198* (2013.01); *A61K 31/455* (2013.01)

(58) Field of Classification Search
CPC .......................... A61K 31/201; A61K 31/202
USPC ......................................................... 514/560
See application file for complete search history.

(56) References Cited

U.S. PATENT DOCUMENTS 10,052,300 B1 * 8/2018 Changaris ............ A61K 31/201 514/355
10,105,332 B1 * 10/2018 Changaris ............ A61K 31/201 514/355

* cited by examiner

*Primary Examiner* — Raymond J Henley, III
(74) *Attorney, Agent, or Firm* — Steve Witters; Witters & Associates (57) ABSTRACT

The present disclosure relates to methods and compositions for suppressing pathogenic bacterial growth, fungal growth, or microbial growth in or on a selected area of skin or open wound. An area of the skin or open wound having pathogenic bacterial growth, fungal growth, or microbial growth is selected for the suppression of the growth. A suppressing material comprising punicic acid is applied to the selected area of the skin and the pathogenic bacterial growth, fungal growth, or microbial growth is suppressed. Methods of making and using the suppressing material comprising punicic acid are also presently provided.

17 Claims, 7 Drawing Sheets

3/4/2017 7:30pm
Before application of CLA-Aspartate-Niacinamide

3/6/2017 11:30 PM
Itching-redness resolved at 24-36 hrs scaling shown at 51 hrs here 3/9/2017 11:30 PM
Subtotal return to normal; salve stopped 5/30/2017 6PM
Resolution of redness persisting after 10weeks

FIG. 13

METHODS AND COMPOSITION FOR SUPPRESSION OF PATHOGENIC BACTERIAL GROWTH, FUNGAL GROWTH, OR MICROBIAL GROWTH IN OR ON SKIN

CROSS-REFERENCE TO RELATED APPLICATIONS

This application is a continuation-in-part (CIP) of U.S. patent application Ser. No. 15/793,978, filed on Oct. 25, 2017, now U.S. Pat. No. 10,105,332 which is a continuation of U.S. patent application Ser. No. 15/788,798, filed on Oct. 19, 2017, now U.S. Pat. No. 10,052,300 both of which are incorporated herein by reference in their entirety.

FIELD OF THE DISCLOSURE

Aspects of the present disclosure generally relate to methods and compositions for suppression of pathogenic bacterial growth, fungal growth, or microbial growth in or on skin.

BACKGROUND

Background information is for informational purposes only and does not necessarily admit that subsequently mentioned information and publications are prior art.

People are cognizant with the notion of microbes (i.e., microorganisms such as bacteria and fungi) as being potentially hazardous and their transmission from person to person. People come into contact with these potentially hazardous microbes on a daily basis. Once in contact with human hands, these microbes or fungi may be passed from individual to individual and, thus, may contribute to the spread of infectious and contagious diseases. One of the most common ways of mitigating infection or transmitting such microbes or fungi is by washing or applying emollients.

SUMMARY

Methods and a composition for suppressing pathogenic bacterial growth, fungal growth, or microbial growth in or on a selected area of skin or open wound comprising punicic acid is provided herein.

According to one aspect of the present disclosure, a method for suppressing pathogenic bacterial growth, fungal growth, or microbial growth in or on a selected area of skin or open wound is provided. The method comprises selecting an area of the skin or open wound having the pathogenic bacterial growth, fungal growth, or microbial growth for the suppression of the pathogenic bacterial growth, fungal growth, or microbial growth. A suppressing material comprising punicic acid is applied to the selected area of the skin or the open wound having the pathogenic bacterial growth, fungal growth, or microbial growth therein or thereon. The pathogenic bacterial growth, fungal growth, or microbial growth in or on the selected area of the skin or the open wound is suppressed for at least 30 minutes.

In another aspect of the present disclosure, a method of making a suppressing material for suppressing pathogenic bacterial growth, fungal growth, or microbial growth in or on a selected area of skin or open wound is provided. The method comprises providing pomegranate oil and adding a metal to the provided pomegranate oil. A reaction of the pomegranate oil with the metal is induced and the reaction forms a substantially clear liquid phase and a colored liquid phase. The substantially clear liquid phase is separated from the colored liquid phase and the suppressing material is provided in the substantially clear liquid phase.

These and other features, aspects and embodiments of the present disclosure will become better understood with reference to the following drawings, description and claims.

DETAILED DESCRIPTION

The following detailed description is not to be taken in a limiting sense, but is made merely for the purpose of illustrating the general principles of the disclosure, since the scope of the disclosure is best defined by the appended claims.

Various inventive features are described below that can each be used independently of one another or in combination with other features. However, any single inventive feature may not address any of the problems discussed above or may only address a subset of the problems discussed above. Further, one or more of the problems discussed above may not be fully addressed by any of the features described below.

*Malassezia* sp. have been associated with atopic dermatitis, seborrheic dermatitis, pityriasis versicolor, and *Malassezia folliculitis*. Among the various species *M. furfur* is associated with pityriasis versicolor, *M. globosa* and *M. restricta* are clinically associated with seborrheic dermatitis or dandruff and *M. pachydermatis* is associated with dermatitis and otitis in dogs and cats. *Malassezia* sp. are ubiquitous across the mammalian microbiome.

In at least one embodiment of the present disclosure, a method for suppressing pathogenic bacterial growth, fungal growth, or microbial growth in or on a selected area of skin or open wound, is disclosed. The method may comprise selecting an area of the skin or open wound having the pathogenic bacterial growth, fungal growth, or microbial growth for the suppression of the pathogenic bacterial growth, fungal growth, or microbial growth. A suppressing material comprising punicic acid may be applied to the selected area of the skin or the open wound having the pathogenic bacterial growth, fungal growth, or microbial growth therein or thereon. The pathogenic bacterial growth, fungal growth, or microbial growth in or on the selected area of the skin or the open wound may be suppressed for at least 30 minutes. The pathogenic bacterial growth, fungal growth, or microbial growth in or on the selected area of the skin or the open wound may be suppressed for at least 72 hours.

The suppressing material may comprise the punicic acid in an amount effective to suppress the growth rate of *Malassezia* sp. The suppressing material may comprise the punicic acid in an amount effective to suppress the growth of atopic dermatitis, seborrheic dermatitis, pityriasis versicolor, or *Malassezia folliculitis*.

The punicic acid may be derived from pomegranate oil. The suppressing material have a metal, for example, the suppressing material may have potassium. The suppressing material may have a concentration of the punicic acid in the suppressing material between about 0.1% to about 70%. The suppressing material may have a concentration of a metal in the suppressing material between about 0.04% to about 25%.

The present disclosure shows that punicic acid has antimicrobial properties. Embodiments of the presently disclosed suppressing material may be void of other or additional active agents, other than, or in addition to punicic acid and metal. For example, the suppressing material may solely have the active agent(s) of punicic acid, or punicic acid and metal. In at least one embodiment of the present disclosure, the suppressing material has an active agent consisting essentially of, or consisting of, punicic acid. In at least one other embodiment of the present disclosure, the suppressing material has active agents consisting essentially of, or consisting of, punicic acid and metal. Punicic acid may be the sole active agent in the suppressing material or the punicic acid and the metal may be the sole active agents in the suppressing material.

A suppressing material for suppressing pathogenic bacterial growth, fungal growth, or microbial growth in or on a selected area of skin or open wound may be made by providing pomegranate oil and adding a metal to the provided pomegranate oil. A reaction of the pomegranate oil with the metal may be induced, forming a substantially clear liquid phase and a colored liquid phase. The substantially clear liquid phase may be separated from the colored liquid phase and the suppressing material may be provided in the substantially clear liquid phase.

In at least one embodiment, a metal salt may be added to the provided pomegranate oil. The metal added to the provided pomegranate oil may comprise potassium. The metal added to the provided pomegranate oil may comprise potassium hydroxide The provided pomegranate oil and the added metal may be provided and added in an amount for forming the substantially clear liquid phase having a concentration of the punicic acid in the suppressing material between about 0.1% to about 15%. The provided pomegranate oil and the added metal may be provided and added in an amount to form the substantially clear liquid phase with a concentration of the metal in the suppressing material between about 0.1% to about 70%.

Aspects of the present disclosure generally relate to methods and compositions for suppressing microbial growth in or on selected areas of the skin. For example, the presently disclosed methods and compositions may be used as an active treatment of seborrheic dermatitis. In at least one embodiment, the presently composition inhibits the growth of *Malassezia*.

*Malassezia* sp. have been associated with atopic dermatitis, seborrheic dermatitis, pityriasis versicolor, and *Malassezia folliculitis*. Among the various species *M. globosa* and *M. restricta* are clinically associated with seborrheic dermatitis or dandruff. *Malassezia* sp. are ubiquitous across the human microbiome. Herein, we disclose the ability of a novel cosmetic formulation or composition to inhibit microbial growth.

The presently disclosed composition may comprise naturally occurring materials. In at least one embodiment, the presently disclosed composition consists only of naturally occurring materials. The composition may comprise a plurality of active materials and a synergistic effect of the active materials may be realized for the suppression of microbial growth.

In at least one embodiment of the present disclosure, a composition for suppressing microbial growth comprises at least one of conjugated linoleic acid and punicic acid. The composition may additionally comprise niacinamide and/or L-aspartic acid. A combination of active ingredients of 1) conjugated linoleic acid and/or punicic acid, 2) niacinamide, and optionally 3) L-aspartic acid, may provide a composition that is effective for suppressing microbial growth. An increased effectiveness of a combination of linoleic acid, punicic acid, niacinamide, and/or L-aspartic acid in suppressing microbial growth may be realized, which may be due to a synergistic effect among the active materials.

Conjugated fatty acids and methods of using as well as methods of preparing materials comprising conjugated fatty acids are disclosed in U.S. Pat. Nos. 7,074,418, 7,897,160 and 9,549,550, each of which are incorporated by reference herein. U.S. Pat. Nos. 9,549,550, 7,897,160, and 7,074,418 are incorporated by reference in their entirety herein, except for the prosecution thereof and words relating to the opinions and judgments of the author and words not directly relating to the technical details of the description of the aspects therein, are not incorporated by reference. The purpose of incorporating these publications is solely to provide additional information relating to technical features of one or more aspects, which information may not be completely disclosed in the wording in the pages of this application. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more aspects, are not to be incorporated by reference herein.

Conjugated fatty acids result from the shift of a double bond in the long chained fatty acid with two double bonds, predominantly in safflower oil and sunflower oil, the diene C18, linoleic acid. The linoleic acid molecule in its natural plant expressed state has two double bonds separated by a single carbon, which is saturated with hydrogen. Thus the molecules C9, C11 and C10, C12 linoleic acids represent two of the most common linoleic acids.

12 11 10 9 linoleic acid

This unconjugated form permits the aliphatic and carboxyl ends to rotate about the C10 or C11. The conjugated form derived from processing has the general formula (C18:2 c9, t11; and C18:2 t10 c12):

conjugated linoleic acid

There are some 28 isomers of CLA. When the double bonds are close as in CLA, the central double bonds resemble a "boomerang" with a hydrophobic center that allows for the orientation of amphipathic molecules and the semi-rigidity of the emulsion. Both cis and trans molecules may contribute to the processes and compositions disclosed herein.

Both CLA and steric acid contain 18 carbons. In general the majority of cell walls are a bi-lipid layer comprised to two adjacent 18 carbon stearic acids. Membranes comprised of both CLA and stearic acid would lack a coherent rigid cell wall essential to the integrity of bacteria and fungi. CLA may have the properties for reducing bacterial and/or fungal growth by interfering with the normal metabolism of C-18 molecules of pathogenic bacteria and fungi.

The CLA of the present disclosure may be esterified with methyl, ethyl, or longer radicals. The CLA of the present disclosure may be sulfated or ethoxylated sulfate or similar negatively charged moiety.

Punicic acid (also called trichosanic acid) is a polyunsaturated fatty acid, 18:3 cis-9, trans-11, cis-13. It is named for the pomegranate and is obtained from pomegranate seed oil. It is also found in the seed oils of snake gourd. Punicic acid is chemically similar to the conjugated linoleic acids, or CLA. Punicic acid has three double bonds whereas CLA has two double bonds. The inventors have discovered that punicic acid has antimicrobial properties.

Niacinamide, also known as nicotinamide (NAA), is a vitamin found in food, used as a dietary supplement, and used as a medication. As a supplement, it is used by mouth to prevent and treat pellagra (niacin deficiency).

L-aspartic acid (L-ASP) is one of the non-essential amino acids in human protein ordinarily used in cosmetic products. L-aspartic acid is found in animals and plants, especially in sugar cane and sugar beets. Aspartic Acid has an overall negative charge and plays an important role in the synthesis of other amino acids and in the citric acid and urea cycles.

In at least one embodiment of the present disclosure, a composition for suppressing microbial growth comprises naturally occurring materials acting as an active treatment. For example, the composition may be used to treat seborrheic dermatitis. The composition may comprise CLA and isomers, or punicic acid, or both. The composition may inhibit the growth of Malassezia species known to cause seborrheic dermatitis or seborrhea. The pharmaceutical product when coupled with a diet rich in conjugated linoleic acid may further reduce the symptoms of skin dermatitis.

The present disclosure relates to a method and pharmacologic preparations, compositions, or natural compositions, which may be used in the dermatologic field to treat seborrheic dermatitis by direct skin application. Seborrhea affects 4-31% of the general population. While no generally agreed upon etiology is accepted, most agree Malassezia species figure prominently in the maintenance of symptoms. This fungus or microbe requires saturated fats to grow. Antifungal agents such as Ketoconazol are the mainstream of treatment for seborrhea.

The presently disclosed compositions and methods show activity against 3 species of Malassezia, namely M. globosa, M. restricta and M. furfur. It is presently disclosed that Nicotinamide (vitamin B3 amide) and aspartic acid (amino acid) have additive capacity in efficacy. It is also presently disclosed that nicotinamide has a direct inhibitory action on Malassezia species. It is presently shown that Aspartic acid alone has specific impact on reducing the growth of three Malassezia species.

In at least one embodiment of the present disclosure, a composition for suppressing microbial growth comprises conjugated linoleic acid, punicic acid, or combination thereof. Aspects of the disclosed composition may comprise Niacinamide and/or L-aspartic acid. The composition may comprise the conjugated linoleic acid, punicic acid, or combination thereof, in a range between about 0.5% to about 70%, or in a range between about 0.5% to about 30%. A balance of the composition may comprise inert or non-acting materials such as water and/or one or more pharmacologically acceptable carriers.

In at least one other embodiment of the present disclosure, a composition for suppressing microbial growth comprises conjugated linoleic acid, Punicic acid, or combination thereof, and optionally, niacinamide and/or L-aspartic acid. The composition may comprise the niacinamide in a range from about 0.1% to about 15%, or in a range from about 0.1% to about 10%. A balance of the composition may comprise inert or non-acting materials such as water and/or one or more pharmacologically acceptable carriers.

In at least one other embodiment of the present disclosure, a composition for suppressing microbial growth comprises conjugated linoleic acid, Punicic acid, or combination thereof; niacinamide; and L-aspartic acid. The composition may comprise the L-aspartic acid in a range from about 0.1% to about 15%, or in a range from about 0.1% to about 10%.

In the following examples, a method for suppressing pathogenic bacterial growth, fungal growth, or microbial growth in or on a selected area of skin or open wound with the application of a suppressing material comprising punicic acid is disclosed. Example 1 shows that punicic acid has antimicrobial properties.

EXAMPLES

Example 1

A suppressing material having punicic acid is shown to inhibit microbial growth. The suppressing material may be a cosmetic formulation and may be herein referred to as P667. For example, the suppressing material may have a concentration of punicic acid between about 0.1% to about 15%.

In Vitro Materials and Methods:

Organisms.

Malassezia strains, M. restricta, M. globosa, M. furfur and M. pachydermatis were obtained from the ATCC. Strain identifications were confirmed using previously established phenotypic culture-based methods. P667 was obtained from Ceela Naturals. All other materials were obtained from HiMedia or Sigma Aldrich unless otherwise mentioned.

Culture Media.

Cultures of Malassezia sp. were grown on Modified Leeming and Notman Agar (MLNA) composed of (per 1 L) Bacteriological peptone (10 g), Glucose (10 g), Yeast extract (2.0 g), desiccated Ox bile (8.0 g), Glycerol (10 mL), Glycerol monostearate (0.5 g), Tween 60 (5.0 mL), Olive oil (20 mL), Agar (15 g) and sterilized by autoclaving. For liquid media, Modified Leeming and Notman Broth (MLNB), agar was omitted. Sabouraud Dextrose Agar (SDA, Acumedia) was used as a negative control. CHROMagarMalassezia media (DRG International, Springfield, N.J.) was used for strain identification.

Procedure.

Experimental solid media was supplemented with 2-10% P667 and assessed for growth after 5 days. All the experiments were performed in triplicate.

Growth curves.

Determination of cell viability was based on cfu/mL from liquid cultures grown at 30° C. with shaking at 150 rpm. A single colony was used to inoculate a 10 mL starter culture in MLNB, which was grown to saturation (5 days). Starter cultures were diluted into a 25 mL MLNB culture to obtain an $OD_{600}$=0.1. Experimental cultures were supplemented with nothing (control) or 10% P667. At appropriate time intervals (0 h, 24 h, 48 h and 72 h) 1 mL aliquots of the cell suspension were withdrawn and plated on MLNA. All the experiments were performed in triplicate.

Figure 1:
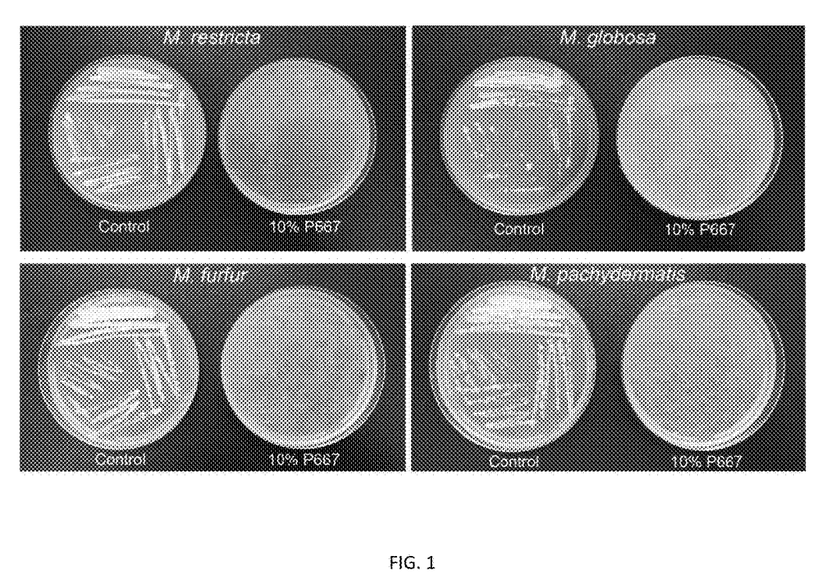
FIG. 1 shows *M. restricta*, *M. globosa*, *M. furfur* and *M. pachydermatis* growth on solid media.

Results:

FIG. 1 shows *M. restricta, M. globosa, M. furfur* and *M. pachydermatis* growth on solid media. Top left panel: *M. restricta* on MLNA media (left) and MLNA media supplemented with 10% (v/v) P667. Top right panel: *M. globosa* on MLNA media (left) and MLNA media supplemented with 10% (v/v) P667. Bottom left panel: *M. furfur* on MLNA media (left) and MLNA media supplemented with 10% (v/v) P667. Bottom right panel: *M. pachydermatis* on MLNA media (left) and MLNA media supplemented with 10% (v/v) P667. Only *M. pachydermatis* can slightly grow on P667 supplemented media.

Figure 2:
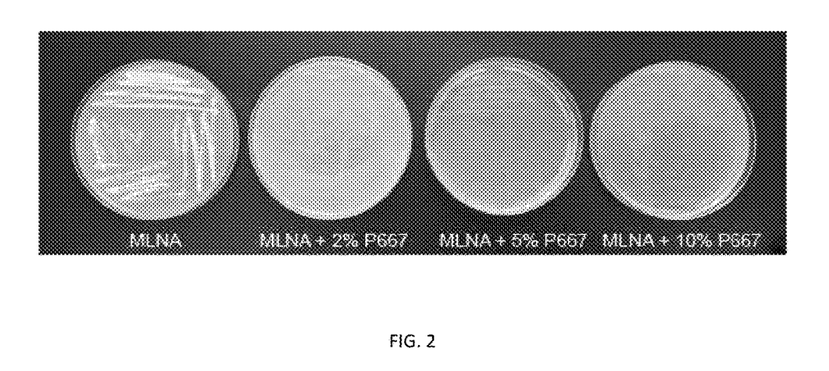
FIG. 2 shows *M. restricta* growth on solid media.
Figure 3:
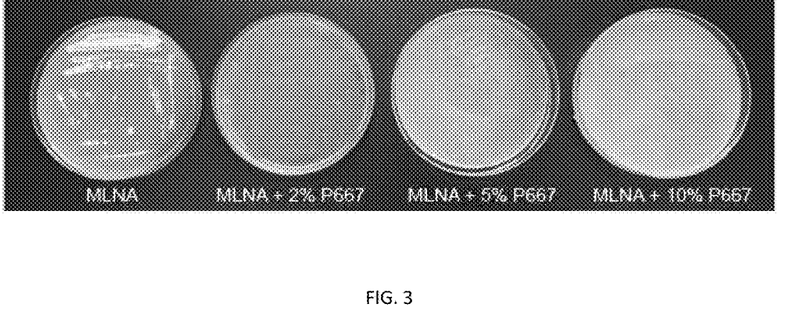
FIG. 3 shows *M. globosa* growth on solid media.
Figure 4:
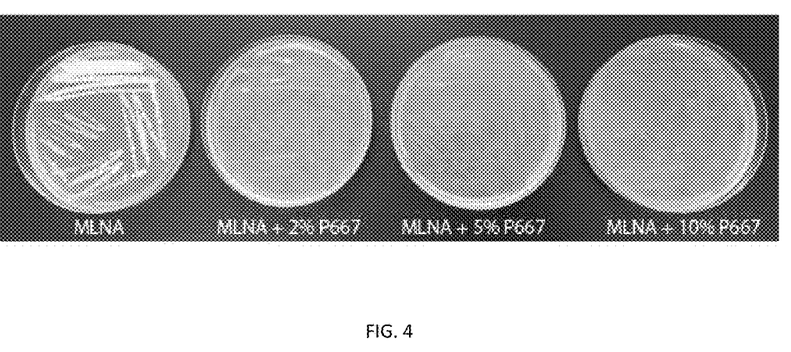
FIG. 4 shows *M. furfur* growth on solid media.

FIG. 2 shows *M. restricta* growth on solid media. Only slight growth is observed on MLNA+2% P667 supplemented media. FIG. 3 shows *M. globosa* growth on solid media. *M. globosa* growth was not observed on any concentration of P667 tested. FIG. 4 shows *M. furfur* growth on solid media. Only slight growth is observed on MLNA+2% and 5% P667 supplemented media.

Figure 5:
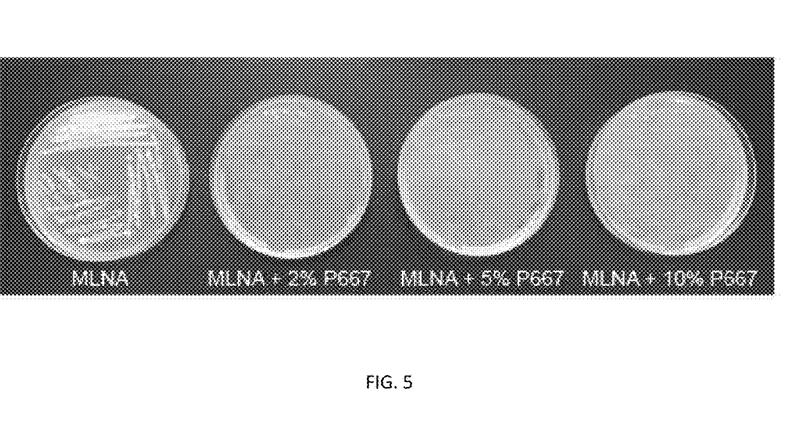
FIG. 5 shows *M. pachydermatis* growth on solid media.
Figure 6:
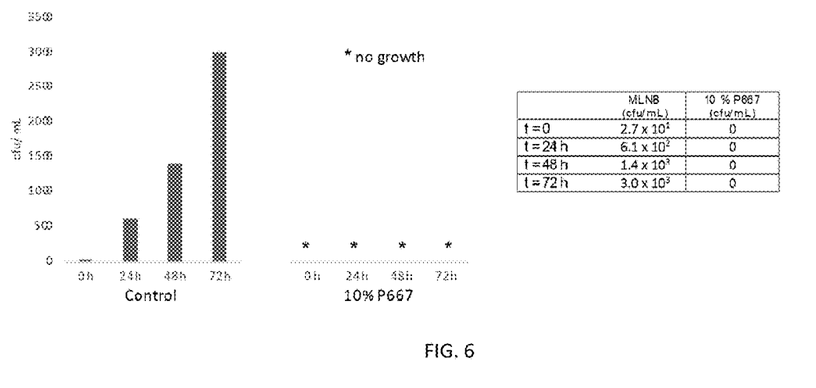
FIG. 6 shows *M. restricta* growth in liquid MLNB media.
Figure 7:
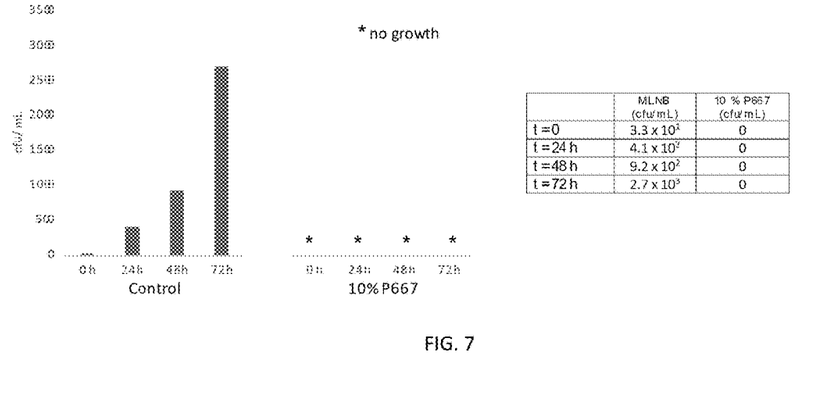
FIG. 7 shows *M. globosa* growth in liquid MLNB media.

FIG. 5 shows *M. pachydermatis* growth on solid media. Slight growth is observed on all concentrations of MLNA+P667 supplemented media. FIG. 6 shows *M. restricta* growth in liquid MLNB media. Only averaged cfu/mL is shown. *M. restricta* on MLNA media (left) and MLNA media supplemented with 10% (w/v) P667. Growth is inhibited in P667 supplemented media. FIG. 7 shows *M. globosa* growth in liquid MLNB media. Only averaged cfu/mL is shown. *M. globosa* on MLNA media (left) and MLNA media supplemented with 10% (w/v) P667. Growth is inhibited in P667 supplemented media.

Figure 8:
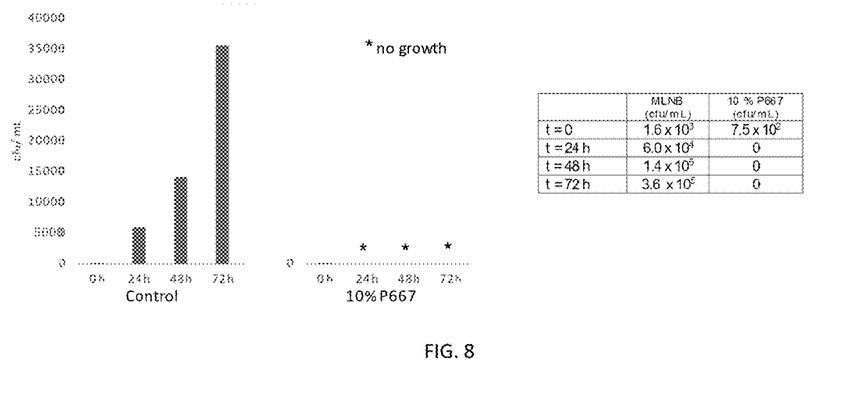
FIG. 8 shows *M. furfur* growth in liquid MLNB media.
Figure 9:
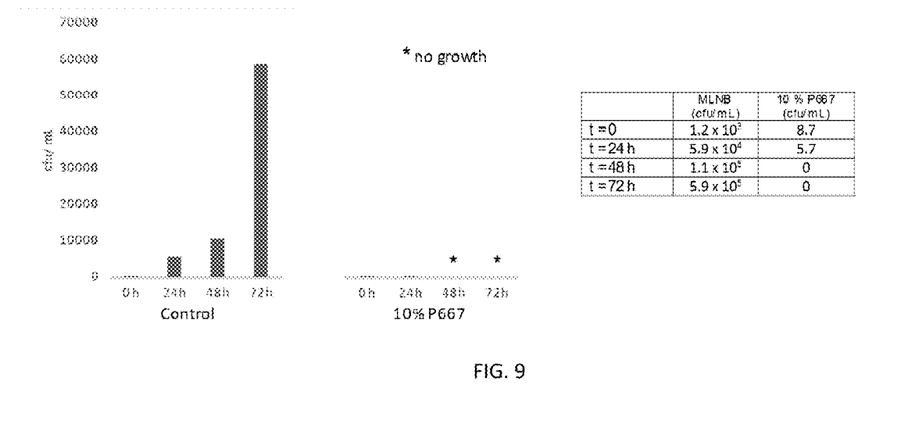
FIG. 9 shows *M. pachydermatis* growth in liquid MLNB media.

FIG. 8 shows *M. furfur* growth in liquid MLNB media. Only averaged cfu/mL is shown. *M. furfur* on MLNA media (left) and MLNA media supplemented with 10% (w/v) P667. Growth is inhibited after 24 h in P667 supplemented media. FIG. 9 shows *M. pachydermatis* growth in liquid MLNB media. Only averaged cfu/mL is shown. *M. pachydermatis* on MLNA media (left) and MLNA media supplemented with 10% (w/v) P667. Growth is inhibited after 24 h in P667 supplemented media.

CONCLUSION

*M. globosa, M. restricta* and *M. furfur* growth is completely inhibited by a 10% (w/v) supplementation of P667 (FIGS. 1-4 and 6-8). The lowest effective concentration of P667 is 2% (w/v). *M. pachydermatis* growth is strongly suppressed by a 10% (w/v) supplementation of P667 (FIGS. 1, 5 and 9). A 10% concentration of P667 is sufficient to inhibit the growth of *M. globosa, M. restricta, M. furfur* and *M pachydermatis* in vitro.

A method of making a suppressing material having punicic acid for suppressing pathogenic bacterial growth, fungal growth, or microbial growth in or on a selected area of skin or open wound is presently disclosed. The method may be similar to a process of making soap and may exclude a step eliminating glycerol. For example, potassium hydroxide may be added to pomegranate oil. Upon waiting, two phases may appear. A clear phase may comprise the suppressing material. The potassium hydroxide may be first added to water and then added to pomegranate oil. In another embodiment, phosphoric acid may be added to pomegranate oil to generate punicic acid which may which may be used as a component of the presently disclosed suppressing material having punicic acid.

In at least one embodiment of the present disclosure, a method of making a suppressing material for suppressing pathogenic bacterial growth, fungal growth, or microbial growth in or on a selected area of skin or open wound comprises providing pomegranate oil and adding a metal to the provided pomegranate oil. A reaction of the pomegranate oil with the metal may be induced, forming a substantially clear liquid phase and a colored liquid phase. The substantially clear liquid phase may be separated from the colored liquid phase and the suppressing material may be in the substantially clear liquid phase.

The metal added to the provided pomegranate oil may have a potassium metal and/or a metal salt. For example, potassium hydroxide may be added to the provided pomegranate oil. The substantially clear liquid phase may have a concentration of the punicic acid in the suppressing material between about 0.1% to about 15%. The metal may be added in an amount to form the substantially clear liquid phase with a concentration of the metal in the suppressing material between about 0.1% to about 70%.

Example 2

A method for making a suppressing material having punicic acid is performed by providing: Pomegranate oil 100 g, Potassium hydroxide 50 g, and Water qs tp 1000 g. The potassium hydroxide may be added to the water and the potassium hydroxide and water mixture may be added to the pomegranate oil to form a solution. The solution is heated to about 160 deg F. for about 24 hours. The solution is cooled to about 100 deg F. Phoshoric acid is added to the solution in an amount to obtain a pH of about 6 in the solution. The solution is heat to about 180 deg F. for about 24 hours and two liquid phases may be formed. The top, substantially clear, oil layer, is separated from the colored liquid phase. The substantially clear liquid phase is cooled and mechanically dry. Free punicic acid having a concentration of about 74%, by free fatty acid analysis, may be provided. This example may provide substantially pure metal salts of punicic acid.

Example 3

In Vitro Materials and Methods:

Organisms.

*Malassezia* strains, *M. restricta* MYA-4611 and *M. globosa*, were obtained from American Type Culture Collection, ATCC, of Manassas, Va. Strain identifications were confirmed using previously established phenotypic culture-based methods. The presently disclosed composition was obtained from Ceela Naturals, of Louisville, Ky. All other materials were obtained from HiMedia or Sigma Aldrich unless otherwise mentioned.

Culture Media.

Cultures of *M. restricta* and *M. globosa* were grown on Modified Leeming and Notman Agar (MLNA) composed of (per 1 L) Bacteriological peptone (10 g), Glucose (10 g), Yeast extract (2.0 g), desiccated Ox bile (8.0 g), Glycerol (10 mL), Glycerol monostearate (0.5 g), Tween 60 (5.0 mL), Olive oil (20 mL), Agar (15 g) and sterilized by autoclaving. For liquid media, Modified Leeming and Notman Broth (MLNB), agar was omitted. Sabouraud Dextrose Agar (SDA, Acumedia) was used as a negative control. CHROMagarMalassezia media (DRG International, Springfield, N.J.) was used for strain identification.

Procedure.

Experimental solid media was supplemented with 2%-10% of an embodiment of the presently disclosed composition. In the present example, an example composition comprising 0.5% niacinamide (Pure Bulk), 0.46% L-Asp (Pure Bulk), and 1.5% conjugated linoleic acid (Stepan) was prepared and used. Separately, experimental solid media were individually supplemented 0.5% niacinamide, 0.46% L-Asp, and 1.5% conjugated linoleic acid. Additionally, a control solid media was not supplemented. The control and supplemented media were assessed for growth after 5 days. All experiments were performed in triplicate.

Determination of cell viability was based on cfu/mL from liquid cultures grown at 30° C. with shaking at 150 rpm. A single colony was used to inoculate a 10 mL starter culture in MLNB, which was grown to saturation (5 days). Starter cultures were diluted into a 125 mL MLNB culture to obtain an $OD_{600}$=0.1. Experimental cultures were supplemented with nothing (control), 2%-10% of the example composition, 0.5% niacinamide, 0.46% L-Asp, or 1.5% conjugated linoleic acid. At appropriate time intervals (0 h, 24 h, 48 h, 72 h, and 168 h) 1 mL aliquots of the cell suspension were withdrawn and plated on MLNA. All the experiments were performed in duplicate.

Figure 10:
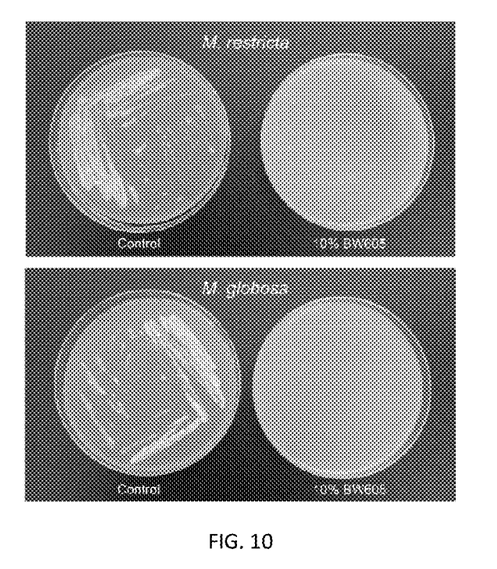
FIG. 10 shows *M. restricta* and *M. globosa* growth on solid media.
Figure 11:
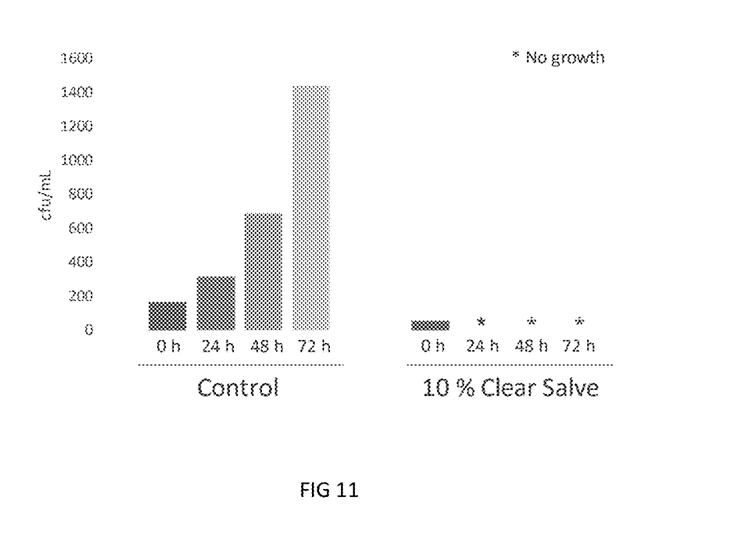
FIG. 11 shows *M. restricta* and *M. globosa* growth in liquid MLNB media.

Results:

FIGS. 10 and 11 show that *M. globosa* and *M. restricta* are inhibited by a 10% (v/v) supplementation of the example composition. The lowest effective concentration of the example composition was shown to be 5% (v/v). Specifically FIG. 10 shows *M. restricta* and *M. globosa* growth on solid media. Top panel: *M. restricta* on MLNA media (left) and MLNA media supplemented with 10% (v/v) of the example composition (right). Bottom panel: *M. globosa* on MLNA media (left) and MLNA media supplemented with 10% (v/v) of the example composition. FIG. 10 shows that neither *Malassezia* sp. can grow on the example composition supplemented media.

Specifically, FIG. 11 shows *M. restricta* and *M. globosa* growth in liquid MLNB media. Only averaged cfu/mL of both *Malassezia* sp. is shown. Growth was measured at the selected time intervals of 0, 24 hours, 48 hours, and 72 hours. The graph on the left shows that exponential growth was exhibited in the control having no supplementation. The graph on the right shows that the sample having a 10% supplementation of the example composition exhibited no growth after 24 hours.

Figure 12:
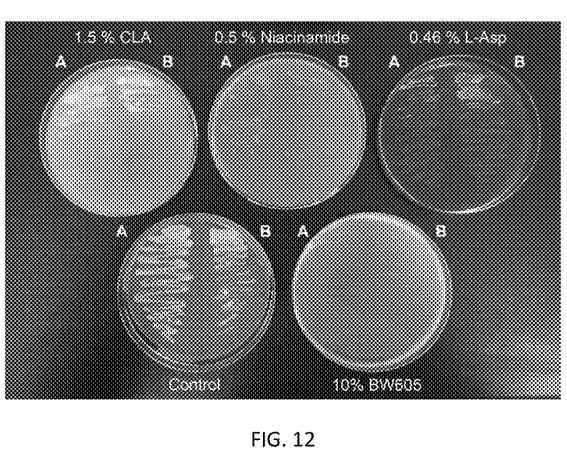
FIG. 12 shows *M. restricta* and *M. globosa* growth on solid media with composition and individual component supplementation.

The synergistic effect of ingredients in the example composition is shown to provide effective inhibition. As shown in FIG. 12 and Tables 1 and 2, below, each component alone may not be sufficient to fully suppress growth on solid or liquid media.

FIG. 12 shows *M. restricta* and *M. globosa* growth on solid media with individual component supplementation of 1.5% CLA, 0.5% niacinamide, and 0.46% L-Asp, top row respectively. A) is the left portion of the plate with *M. restricta* and B) is the right portion of the plate having *M. globosa*. All individual components support some growth as shown in the plates in the top row of FIG. 12. The 10% (v/v) supplementation of the example composition shows that example composition does not support growth as shown in the bottom right plate in FIG. 12.

The bottom left plate is the control having no supplementation and shows substantially more growth than each of the other plates.

TABLE 1

*M. restricta* growth in liquid MLNB media.

| | MLNB (cfu/mL) | 10% THE PRESENTLY DISCLOSED COMPOSITION (cfu/mL) | 0.5% Niacinamide (cfu/mL) | 0.46% L-Asp (cfu/mL) | 1.5% CLA (cfu/mL) |
|---|---|---|---|---|---|
| t = 0 | $2.5 \times 10^2$ | | | | |
| t = 24 h | $4.6 \times 10^2$ | 0 | 20 | 15 | 7 |
| t = 48 h | $8.5 \times 10^2$ | 0 | 5 | 11 | 0 |
| t = 72 h | $1.7 \times 10^3$ | 0 | 0 | 10 | 0 |
| t = 168 h | $2.0 \times 10^5$ | 0 | 0 | 14 | 0 |

TABLE 2

*M. globosa* growth in liquid MLNB media.

| | MLNB (cfu/mL) | 10% THE PRESENTLY DISCLOSED COMPOSITION (cfu/mL) | 0.5% Niacinamide (cfu/mL) | 0.46% L-Asp (cfu/mL) | 1.5% CLA (cfu/mL) |
|---|---|---|---|---|---|
| t = 0 | $1.1 \times 10^2$ | | | | |
| t = 24 h | $2.4 \times 10^2$ | 0 | 2 | 14 | 2 |
| t = 48 h | $6.4 \times 10^2$ | 0 | 0 | 10 | 0 |
| t = 72 h | $1.2 \times 10^3$ | 0 | 0 | 6 | 0 |
| t = 168 h | $2.2 \times 10^5$ | 0 | 0 | 1 | 0 |

CONCLUSION

A supplementation of a 10% concentration of the example composition comprising 1.5% CLA, 0.5% niacinamide (Pure Bulk), and 0.46% L-Asp (Pure Bulk) is sufficient to inhibit the growth of *M. globosa* and *M. restricta* in vitro.

Example 4

In Vivo

A first test composition comprising 15% CLA and 4.6% L-Asp was prepared. An area of the skin of a subject having the microbial growth was selected. The first test composition was applied onto the selected area of skin daily and the subject was examined at selected time intervals. After 10 days, the subject exhibited no visual change as shown in the upper left of FIG. 13.

A second test composition comprising 15% CLA, 5% niacinamide, and 4.6% L-Asp was prepared. The same area of the skin of the same subject having the microbial growth was selected, like the application of the first test composition. The second test composition was applied in the same manner as the first composition and the subject was again examined at selected time intervals. The results are shown in FIG. 13.

Figure 13:
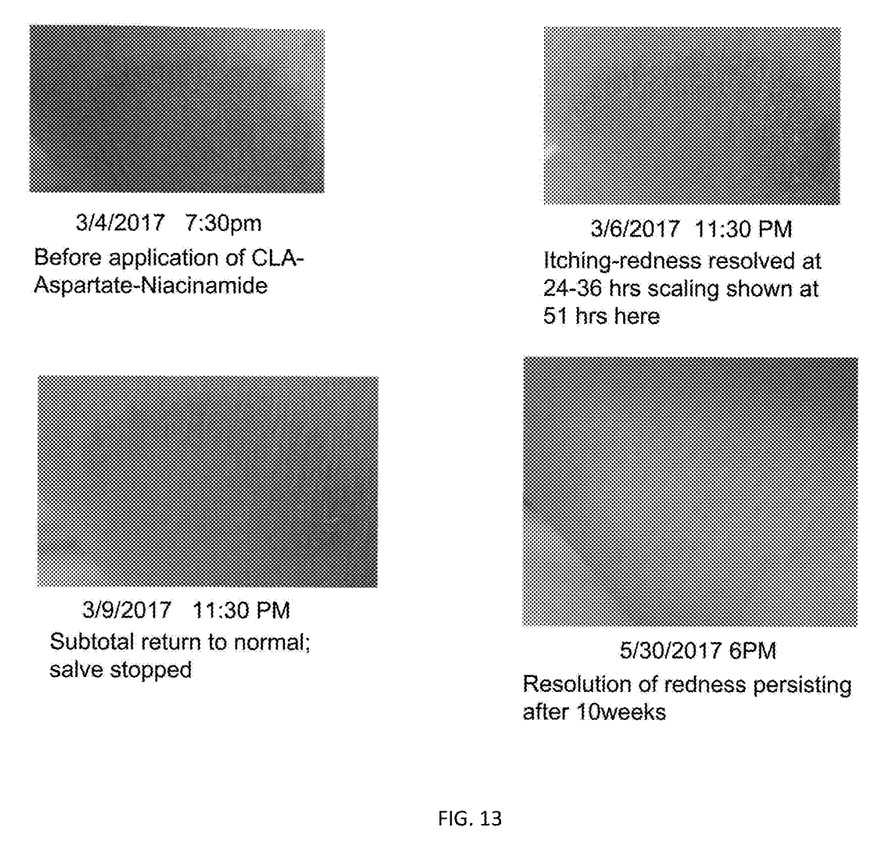
FIG. 13 shows in vivo results of an application of the presently disclosed composition.

With the application of the second composition having CLA, niacinamide, and L-Asp, the subject showed a clear reduction in itching and burning at 24 hours or less and clear visual evidence of healing is shown in FIG. 13, upper right, at 51 hours or less. The subject returned to normal in about 5 days, as shown in the lower left picture in FIG. 13, and the resolution of fungal growth persisted, as shown in the lower right picture in FIG. 13.

The results of the application of the first composition compared with the application of the second composition demonstrates the synergistic effect of CLA, niacinamide, and L-Asp with the in vivo application.

It should be understood that the foregoing relates to exemplary aspects of the disclosure and that modifications may be made without departing from the spirit and scope of the disclosure as set forth in the following claims.

The invention claimed is:

1. A method for suppressing pathogenic bacterial growth, fungal growth, or microbial growth in or on a selected area of skin or open wound, the method comprising the steps of:
   selecting an area of the skin or open wound having the pathogenic bacterial growth, fungal growth, or microbial growth for the suppression of the pathogenic bacterial growth, fungal growth, or microbial growth;
   applying a suppressing material comprising punicic acid to the selected area of the skin or the open wound having the pathogenic bacterial growth, fungal growth, or microbial growth therein or thereon; and
   suppressing the pathogenic bacterial growth, fungal growth, or microbial growth in or on the selected area of the skin or the open wound for at least 30 minutes.

2. The method of claim 1, wherein the punicic acid is the sole active agent in the suppressing material.

3. The method of claim 1, wherein the suppressing material comprises punicic acid and a metal, the punicic acid and the metal are the sole active agents in the suppressing material.

4. The method of claim 1, wherein the suppressing material suppresses the pathogenic bacterial growth, fungal growth, or microbial growth in or on the selected area of the skin or the open wound for at least 72 hours.

5. The method of claim 1, wherein the suppressing material comprises the punicic acid in an amount effective to suppress the growth rate of *Malassezia* sp.

6. The method of claim 1, wherein the suppressing material comprises the punicic acid in an amount effective to suppress the growth of atopic dermatitis, seborrheic dermatitis, pityriasis versicolor, or *Malassezia folliculitis*.

7. The method of claim 1, wherein the punicic acid is derived from pomegranate oil.

8. The method of claim 1, wherein the suppressing material further comprises a metal.

9. The method of claim 8, wherein the metal is potassium.

10. The method of claim 1, wherein the concentration of the punicic acid in the suppressing material is between about 0.1% to about 70%.

11. The method of claim 8, wherein the concentration of the metal in the suppressing material is between about 0.04% to about 25%.

12. A method of making a suppressing material for suppressing pathogenic bacterial growth, fungal growth, or microbial growth in or on a selected area of skin or open wound comprising the steps of:
    providing pomegranate oil;
    adding a metal to the provided pomegranate oil;
    inducing a reaction of the pomegranate oil with the metal and forming a substantially clear liquid phase and a colored liquid phase; and
    separating the substantially clear liquid phase from the colored liquid phase and providing the suppressing material in the substantially clear liquid phase.

13. The method of making a suppressing material of claim 12, wherein the step of adding a metal to the provided pomegranate oil comprises adding a potassium to the provided pomegranate oil.

14. The method of making a suppressing material of claim 12, wherein the step of adding a metal to the provided pomegranate oil comprises adding a metal salt to the provided pomegranate oil.

15. The method of making a suppressing material of claim 14, wherein the step of adding a metal salt to the provided pomegranate oil comprises adding potassium hydroxide to the provided pomegranate oil.

16. The method of making a suppressing material of claim 12, wherein the provided pomegranate oil and the added metal are provided and added in an amount for forming the substantially clear liquid phase having a concentration of the punicic acid in the suppressing material between about 0.1% to about 15%.

17. The method of making a suppressing material of claim 12, wherein the provided pomegranate oil and the added metal are provided and added in an amount to form the substantially clear liquid phase with a concentration of the metal in the suppressing material between about 0.1% to about 70%.

\* \* \* \* \*